(12) United States Patent
Keilhack et al.

(10) Patent No.: US 11,642,347 B2
(45) Date of Patent: May 9, 2023

(54) EZH2 INHIBITORS FOR TREATING LYMPHOMA

(71) Applicants: Epizyme, Inc., Cambridge, MA (US); Eisai R&D Management Co., Ltd., Tokyo (JP)

(72) Inventors: Heike Keilhack, Belmont, MA (US); Sarah K. Knutson, Lincoln, MA (US); Danielle Johnston Blackwell, Cambridge, MA (US); Larisa Reyderman, Watchung, NJ (US); Lone Ottesen, London (GB)

(73) Assignees: Epizyme, Inc., Cambridge, MA (US); Eisai R&D Management Co., Ltd., Tokyo (JP)

( * ) Notice: Subject to any disclaimer, the term of this patent is extended or adjusted under 35 U.S.C. 154(b) by 294 days.

(21) Appl. No.: 16/808,513

(22) Filed: Mar. 4, 2020

(65) Prior Publication Data

US 2020/0323866 A1 Oct. 15, 2020

Related U.S. Application Data

(63) Continuation of application No. 16/454,835, filed on Jun. 27, 2019, now abandoned, which is a continuation of application No. 16/181,747, filed on Nov. 6, 2018, now abandoned, which is a continuation of application No. 15/319,535, filed as application No. PCT/US2015/036310 on Jun. 17, 2015, now Pat. No. 10,166,238.

(60) Provisional application No. 62/036,265, filed on Aug. 12, 2014, provisional application No. 62/013,522, filed on Jun. 17, 2014.

(51) Int. Cl.
| *A61P 35/02* | (2006.01) |
| *A61K 31/4412* | (2006.01) |
| *A61K 31/5377* | (2006.01) |
| *C07D 213/65* | (2006.01) |
| *C07D 405/12* | (2006.01) |
| *A61K 31/4545* | (2006.01) |

(52) U.S. Cl.
CPC ...... *A61K 31/5377* (2013.01); *A61K 31/4412* (2013.01); *A61K 31/4545* (2013.01); *C07D 213/65* (2013.01); *C07D 405/12* (2013.01)

(58) Field of Classification Search
CPC .. A61K 31/4412; A61K 31/5377; A61P 35/02
See application file for complete search history.

(56) References Cited

U.S. PATENT DOCUMENTS

| 8,410,088 B2 | 4/2013 | Kuntz et al. |
| 8,691,507 B2 | 4/2014 | Copeland et al. |
| 8,765,732 B2 | 7/2014 | Kuntz et al. |
| 8,895,245 B2 | 11/2014 | Copeland et al. |
| 9,090,562 B2 | 7/2015 | Kuntz et al. |
| 9,175,331 B2 | 11/2015 | Kuntz et al. |
| 9,333,217 B2 | 5/2016 | Copeland et al. |
| 9,334,527 B2 | 5/2016 | Kuntz et al. |
| 9,522,152 B2 | 12/2016 | Kuntz et al. |
| 9,549,931 B2 | 1/2017 | Kuntz et al. |
| 9,688,665 B2 | 6/2017 | Knutson et al. |
| 10,162,176 B2 | 12/2018 | Yamakawa et al. |
| 10,166,238 B2 | 1/2019 | Keilhack et al. |
| 10,463,671 B2 | 11/2019 | Keilhack et al. |
| 11,202,781 B2 | 12/2021 | Keilhack et al. |
| 2012/0264734 A1 | 10/2012 | Kuntz et al. |
| 2013/0040906 A1 | 2/2013 | Kuntz et al. |
| 2013/0303555 A1 | 11/2013 | Copeland et al. |
| 2014/0120083 A1 | 5/2014 | Stern et al. |
| 2014/0128393 A1 | 5/2014 | Knutson et al. |
| 2015/0051163 A1 | 2/2015 | Keilhack et al. |
| 2015/0283142 A1 | 10/2015 | Stern et al. |
| 2016/0303135 A1 | 10/2016 | Keilhack et al. |
| 2017/0065600 A1 | 3/2017 | Kuntz et al. |
| 2017/0065628 A1 | 3/2017 | Copeland et al. |
| 2017/0233927 A1 | 8/2017 | Lee |
| 2017/0360795 A1 | 12/2017 | Stern et al. |
| 2018/0280402 A1 | 10/2018 | Keilhack et al. |
| 2018/0311251 A1 | 11/2018 | Keilhack et al. |
| 2019/0000860 A1 | 1/2019 | Bradner |
| 2019/0175604 A1 | 6/2019 | Keilhack et al. |
| 2019/0255060 A1 | 8/2019 | Keilhack et al. |
| 2020/0022987 A1 | 1/2020 | Keilhack et al. |
| 2020/0113911 A1 | 4/2020 | Keilhack et al. |
| 2022/0175789 A1 | 6/2022 | Keilhack et al. |
| 2022/0226336 A1 | 7/2022 | Keilhack et al. |

FOREIGN PATENT DOCUMENTS

| WO | WO 2012/034132 A2 | 3/2012 |
| WO | WO 2012/118812 A2 | 9/2012 |
| WO | WO 2012/142504 A1 | 10/2012 |

(Continued)

OTHER PUBLICATIONS

Advani, R.H. et al. (Jan. 2013) "Bruton tyrosine kinase inhibitor ibrutinib (PCI-32765) has significant activity in patients with relapsed/refractory B-cell malignancies" *J Clin Oncol*, 31(1):88-94.

Brunton, L. et al. (Eds.) "Antineoplastic Agents" Chapter 51 in *Goodman & Gilman's Manual of Pharmacology and Therapeutics*. McGraw-Hill Medical, 2008; pp. 853-861 (eBook). EBSCO Publishing: eBook Collection (EBSCOhost), retrieved on Dec. 21, 2015.

(Continued)

*Primary Examiner* — Jeffrey S Lundgren
*Assistant Examiner* — Chris E Simmons
(74) *Attorney, Agent, or Firm* — Cooley LLP; Heidi A. Erlacher; Christine E. Dunne

(57) ABSTRACT

The present invention relates to compositions comprising inhibitors of human histone methyltransferase EZH2 and their use for the treatment of cancer.

10 Claims, 11 Drawing Sheets

(56) References Cited

FOREIGN PATENT DOCUMENTS

| WO | WO 2012/142513 A1 | 10/2012 |
|---|---|---|
| WO | WO 2013/049770 A2 | 4/2013 |
| WO | WO 2013/138361 A1 | 9/2013 |
| WO | WO 2013/155317 A1 | 10/2013 |
| WO | WO 2013/155464 A1 | 10/2013 |
| WO | WO 2013/173441 A2 | 11/2013 |
| WO | WO 2014/062720 A2 | 4/2014 |
| WO | WO 2014/062732 A1 | 4/2014 |
| WO | WO 2014/062733 A2 | 4/2014 |
| WO | WO 2014/071109 A1 | 5/2014 |
| WO | WO 2014/100080 A1 | 6/2014 |
| WO | WO 2014/100646 A1 | 6/2014 |
| WO | WO 2014/100665 A1 | 6/2014 |
| WO | WO 2014/144747 A1 | 9/2014 |
| WO | WO 2014/172044 A1 | 10/2014 |
| WO | WO 2014/194254 A1 | 12/2014 |
| WO | WO 2015/010049 A1 | 1/2015 |
| WO | WO 2015/010078 A2 | 1/2015 |
| WO | WO 2015/057859 A1 | 4/2015 |
| WO | WO 2015/058125 A1 | 4/2015 |
| WO | WO 2015/085325 A1 | 6/2015 |
| WO | WO-2015195848 A1 | 12/2015 |
| WO | WO 2016/201328 A1 | 12/2016 |

OTHER PUBLICATIONS

ClinicalTrials.gov (Dec. 14, 2018) "Open-Label, Multicenter, Phase 1/2 Study of Tazemetostat (EZH2 Histone Methyl Transferase [HMT] Inhibitor) as a Single Agent in Subjects With Advanced Solid Tumors or With B-cell Lymphomas and Tazemetostat in Combination With Prednisolone in Subjects With DLBCL" Bethesda (MD): National Library of Medicine (US). Identifier: NCT01897571 [online]. Retrieved from: clinicaltrials.gov/ct2/show/NCT01897571; retrieved on Jan. 1, 2019, 6 pages.

ClinicalTrials.gov archive (Dec. 11, 2013) "View of NCT01897571 on Dec. 11, 2013. An Open-Label, Multicenter, Phase 1/2 Study of E7438 (EZH2 Histone Methyl Transferase [HMT] Inhibitor) as a Single Agent in Subjects With Advanced Solid Tumors or With B-Cell Lymphomas" Clinical Trials Identifier: NCT01897571, submitted on Dec. 10, 2013 [online]. Retrieved from: https://clinicaltrials.gov/ct2/history/NCT018975717V_4=View#StudyPageTop; retrieved on Jan. 23, 2020; 10 pages.

ClinicalTrials.gov archive (Aug. 21, 2014) "View of NCT01897571 on Aug. 21, 2014. An Open-Label, Multicenter, Phase 1/2 Study of E7438 (EZH2 Histone Methyl Transferase [HMT] Inhibitor) as a Single Agent in Subjects With Advanced Solid Tumors or With B Cell Lymphomas" Clinical Trials Identifier: NCT01897571 [online]. Retrieved from: https://clinicaltrials.gov/archive/NCT01897571/2014_08_21; 7 pages.

ClinicalTrials.gov archive (Mar. 27, 2014) "View of NCT01897571 on Mar. 27, 2014. An Open-Label, Multicenter, Phase 1/2 Study of E7438 (EZH2 Histone Methyl Transferase [HMT] Inhibitor) as a Single Agent in Subjects With Advanced Solid Tumors or With B Cell Lymphomas" Clinical Trials Identifier: NCT01897571 [online]. Retrieved from: https://clinicaltrials.gov/archive/NCT01897571/2014_03_27; 7 pages.

ClinicalTrials.gov(Mar. 28, 2017) "Open-Label, Multicenter, Phase 1/2 Study of Tazemetostat (EZH2 Histone Methyl Transferase [HMT] Inhibitor) as a Single Agent in Subjects With Advanced Solid Tumors or With B-cell Lymphomas and Tazemetostat in Combination With Prednisolone in Subjects With DLBCL" Clinical Trials Identifier: NCT01897571 [online]. Retrieved from: https://clinicaltrials.gov/ct2/show/NCT01897571; retrieved on Apr. 20, 2017; 5 pages.

ClinicalTrials.gov. (Apr. 5, 2011) "A Phase 1 Study Evaluating the Safety and Pharmacokinetics of ABT-199 in Subjects With Relapsed or Refractory Chronic Lymphocytic Leukemia and Non-Hodgkin Lymphoma" Identifier: NCT01328626; first posted Apr. 5, 2011, accessed Jun. 15, 2021; 10 printed pages.

Cunningham, D. et al. (May 25, 2013) "Rituximab plus cyclophosphamide, doxorubicin, vincristine, and prednisolone in patients with newly diagnosed diffuse large B-cell non-Hodgkin lymphoma: a phase 3 comparison of dose intensification with 14-day versus 21-day cycles" Lancet, 381:1817-1826.

Definition of "R-CHOP", National Cancer Institute Web Site; https://www.cancer.gov/about-cancer/treatment/drugs/R-CHOP; posted Sep. 18, 2009; updated May 29, 2012, 2 pages.

Dyer, M. et al. (1990) "A New Human B-Cell Non-Hodgkin's Lymphoma Cell Line (Karpas 422) Exhibiting Both t(14;18) and t(4;11)Chromosomal Translocations" Blood, vol. 75, No. 3, p. 709-714.

Epizyme, Inc. (Nov. 19, 2014) "Phase 1 Dose Escalation Data for Epizyme EZH2 Inhibitor EPZ-6438 (E7438) Shows Single Agent Activity in B-Cell Non-Hodgkin Lymphomas and Malignant Rhabdoid Tumor" [online]. BusinessWire [online]. Retrieved from: http://www.businesswire.com/news/home/20141119006836/en/Phase-1-Dose-Escalation-Data-Epizyme-EZH2; 4 pages.

Garapaty-Rao, S. et al. (Nov. 21, 2013) "Identification of EZH2 and EZH1 Small Molecule Inhibitors with Selective Impact on Diffuse Large B Cell Lymphoma Cell Growth" Chem Biol, 20:1329-1339.

Hassan, U. et al. (2012) "Prognostic Sub-Grouping of Diffuse Large B-Cell Lymphomas into Germinal Centre And Post Germinal Centre Groups by Immunohistochemistry after 6 Cycles of Chemotherapy" Asian Pacific Journal of Cancer Prevention, vol. 13, p. 1341-1347.

Knutson, S. K. et al. (2012) "A selective inhibitor of EZH2 blocks H3K27 methylation and kills its mutant lymphoma cells," Nature Chemical Biology, 8(1):890-896.

Knutson, S. K. et al. (May 2013) "Durable tumor regression in genetically altered malignant rhabdoid tumors by inhibition of methyltransferase EZH2" PNAS, 110(19):7922-7927.

Knutson, S.K. et al. (Apr. 2014) "Selective Inhibition of EZH2 by EPZ-6438 Leads to Potent Antitumor Activity in EZH2-Mutant Non-Hodgkin Lymphoma" Molecular Cancer Therapeutics, vol. 13, No. 4, pp. 842-854.

Knutson, S.K. et al. (Dec. 10, 2014) "Synergistic Anti-Tumor Activity of EZH2 Inhibitors and Glucocorticoid Receptor Agonists in Models of Germinal Center Non-Hodgkin Lymphomas" PLOS ONE, 9(12):e111840; DOI: 10.1371/journal.pone.0111840; 22 pages.

Lannutti, B.J. et al. (Jan. 2011) "CAL-101, a p110δ selective phosphatidylinositol-3-kinase inhibitor for the treatment of B-cell malignancies, inhibits PI3K signaling and cellular viability" Blood, 117(2):591-594.

McCabe, M. T. et al. (2012) "EZH2 inhibition as a therapeutic strategy for lymphoma with EZH2-activating mutations," Nature, 492:108-112.

Petrich, A. et al. (2012) "Akt Inhibitors MK-2206 and Nelfinavir overcome mTOR inhibitor resistance in DLBCL" Author Manuscript [online]. Retrieved from the Internet: www.clincancerres.aacrjournals.org; retrieved on Nov. 28, 2018, 3 pages. Final publication in: Clin Cancer Res, 18(9):2534-2544.

Qi, W. et al. (2012) "Selective inhibition of Ezh2 by a small molecule inhibitor blocks tumor cells proliferation" Proc Natl Acad Sci USA, vol. 109, No. 52, pp. 21360-21365.

Varambally, S. et al. (Oct. 10, 2002) "The Polycomb Group Protein EZH2 Is Involved in Progression of Prostate Cancer" Nature, 419:624-629.

Xiang, C-Y. et al. (Mar. 2012) "Recent advance in the role of TNF-α in cancer" Chinese Bulletin of Life Sciences, 24(3):250-254 (Chinese with English abstract).

Fig. 1

First-in-human Phase 1 Trial

- EPZ-6438 (tazemetostat): oral dosing from 100 mg to 1600 mg BID
- Population: relapsed or refractory B-cell lymphoma or solid tumors
- Study design: 3+3 dose-escalation
  - Expansion cohorts at 800 mg (n=6 planned) and 1600 mg (n=6 planned)
  - Food effect sub-study at 400 mg (n=12 planned)
- Primary endpoint: determination of RP2D/MTD
- Secondary endpoints: safety, PK, PD and tumor response (every 8 wks)
- Data cut-off: 8-Jun-2015

| Dose (mg BID) | Patients (n=45) | Solid tumors (n=26) | B-cell NHL (n=19) |
|---|---|---|---|
| 100* | 6 | 5 | 1 |
| 200 | 3 | 1 | 2 |
| 400 | 3 | 2 | 1 |
| 800 | 14 | 6 | 8 |
| 1600 | 12 | 8 | 4 |
| Food Effect | 7 | 4 | 3 |

* 2 formulations

Fig. 2

Patient Tumor Types

| | | |
|---|---|---|
| Relapsed or refractory NHL | | n=19 * |
| Diffuse large B-cell lymphoma (DLBCL) | GCB | 4 |
| | non-GCB | 6 |
| | undetermined | 3 |
| Follicular lymphoma (FL) | | 5 |
| Marginal zone lymphoma (MZL) | | 1 |
| Relapsed or refractory solid tumor | | n=26 |
| INI1-deficient tumor | | 10 |
| GI malignancy | | 7 |
| GU malignancy | | 5 |
| Sarcoma | | 3 |
| CNS tumor | | 1 |

\* 14 NHL patients tested to date: 13 WT + 1 mutant by cobas® EZH2 Mutation Test
(in development, Roche Molecular Systems, Inc.)

Fig. 3

NHL Patient Demographics

| Characteristic | | Patients (n=19) n (%) |
|---|---|---|
| Median age, years (range) | | 61 (24 - 84) |
| Sex (M / F) | | 14 (74) / 5 (26) |
| # of prior therapeutic regimens | 1 | 2 (10) |
| | 2 | 1 (5) |
| | 3 | 7 (37) |
| | 4 | 2 (10) |
| | ≥5 | 7 (37) |
| Refractory to last prior regimen | | 7 (37) |
| Prior autologous hematopoietic cell transplant | | 5 (26) |

Fig. 6 n = 45

| | All Events | | Treatment-Related | |
|---|---|---|---|---|
| | All Grades * | Grade ≥3 | All Grades | Grade ≥3 ‡ |
| Any patient with AE | 42 | 13 | 29 | 5 |
| Asthenia | 23 | 1 | 10 | 0 |
| Anorexia | 11 | 2 | 4 | 1 |
| Anemia | 9 | 1 | 4 | 0 |
| Dyspnea | 9 | 0 | 0 | 0 |
| Nausea | 8 | 0 | 6 | 0 |
| Constipation | 7 | 0 | 2 | 0 |
| Vomiting | 6 | 0 | 3 | 0 |
| Thrombocytopenia | 6 | 2 | 4 | 1 |
| Dyspepsia | 5 | 0 | 5 | 0 |
| Muscle spasm | 5 | 0 | 2 | 0 |
| Hypertension | 4 | 1 | 2 | 1 |
| Neutropenia | 2 | 1 | 2 | 1 |
| Transaminase ↑ | 2 | 1 | 1 | 1 |

Patients with:
Dose reduction = 1
Drug discontinuation = 1
Dose interruption = 7

\* >10% of patients
‡ all patients

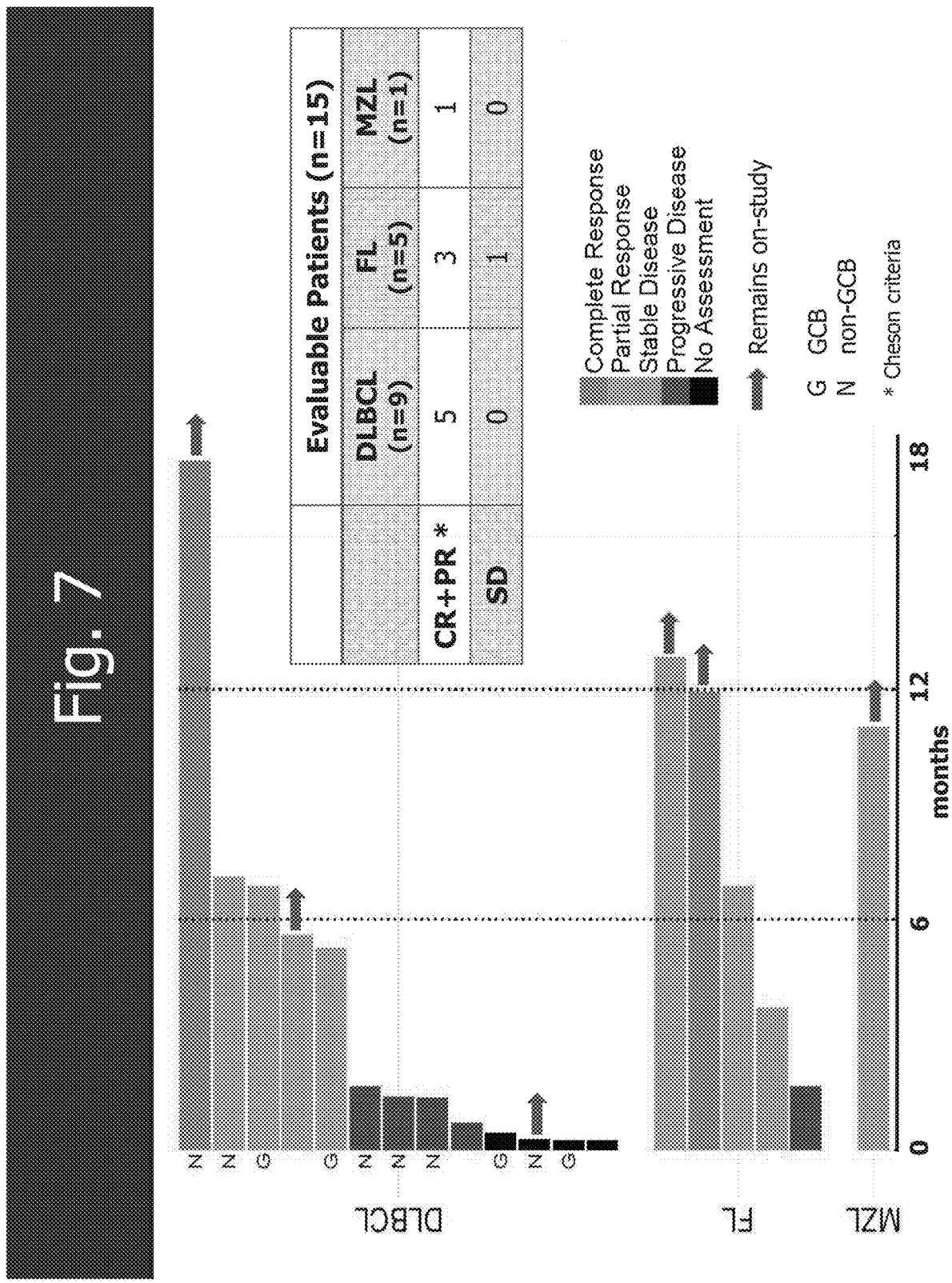

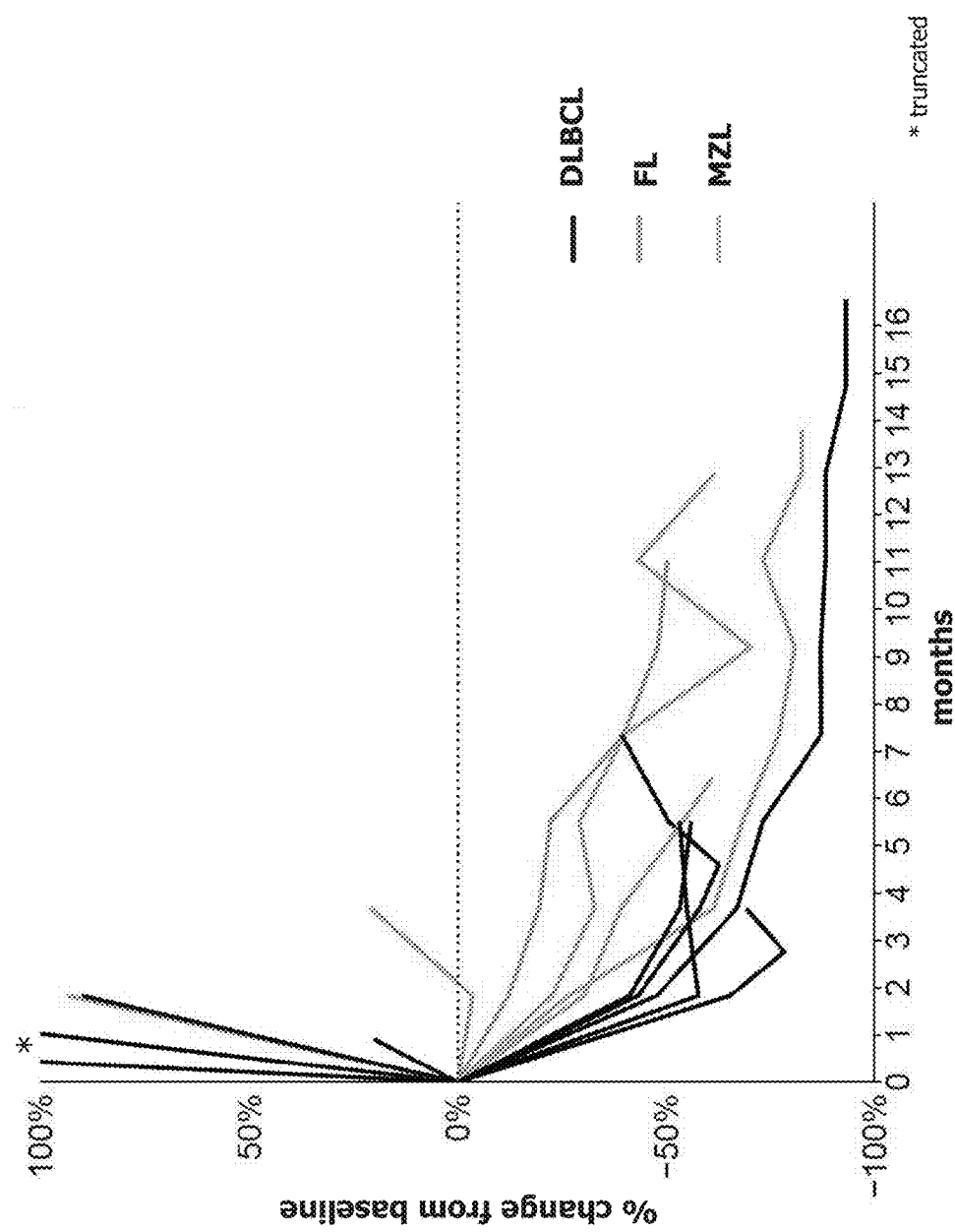

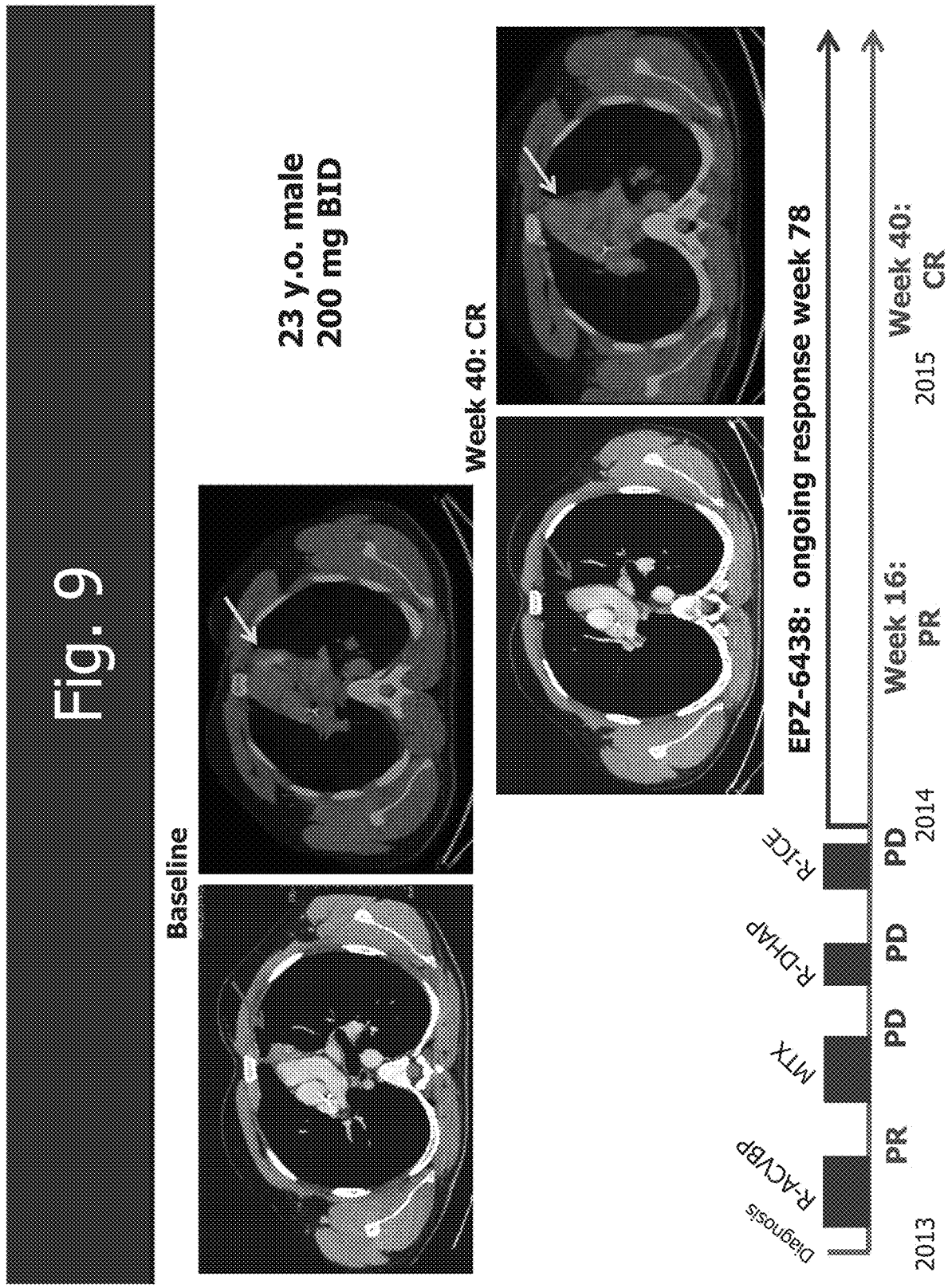

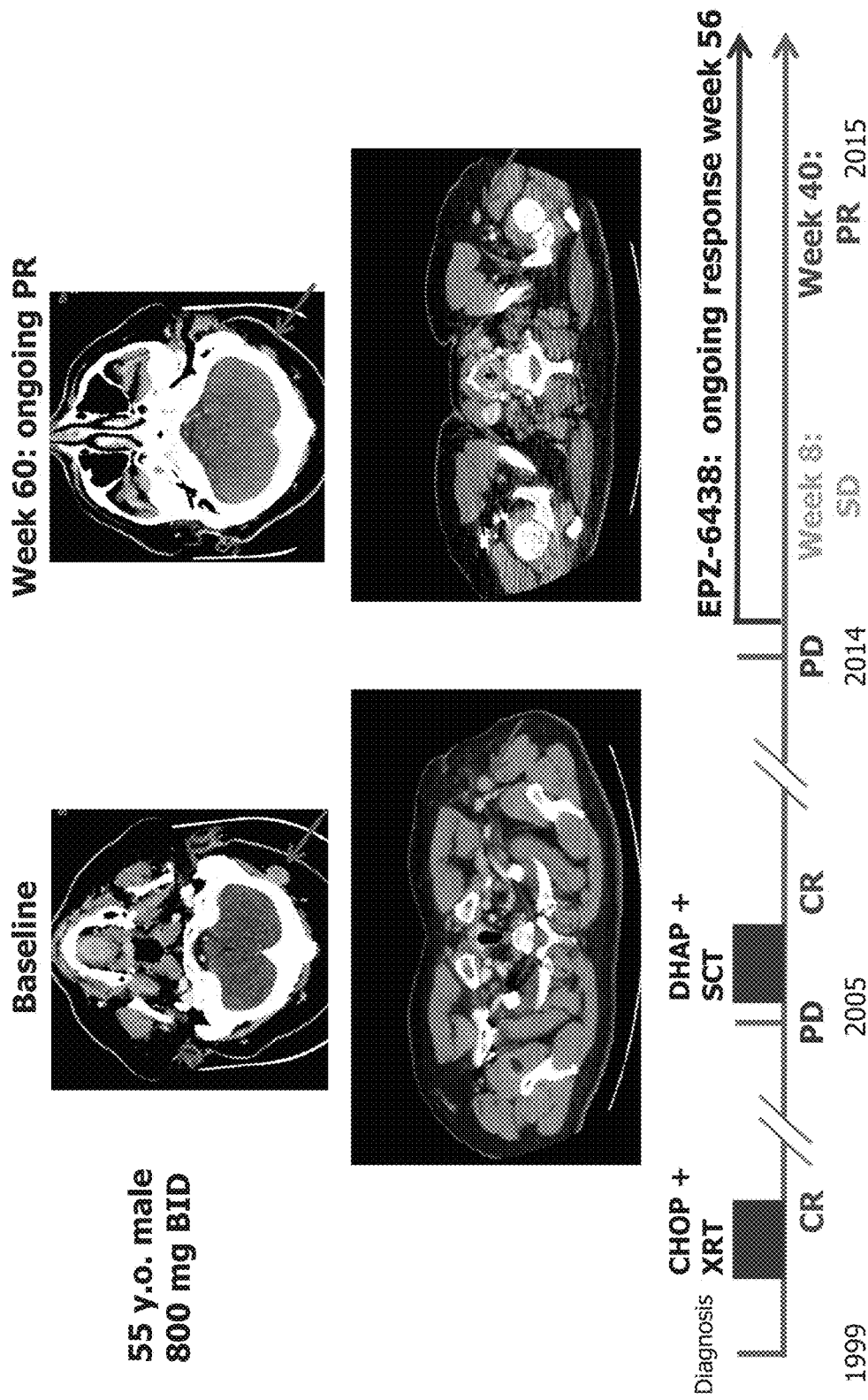

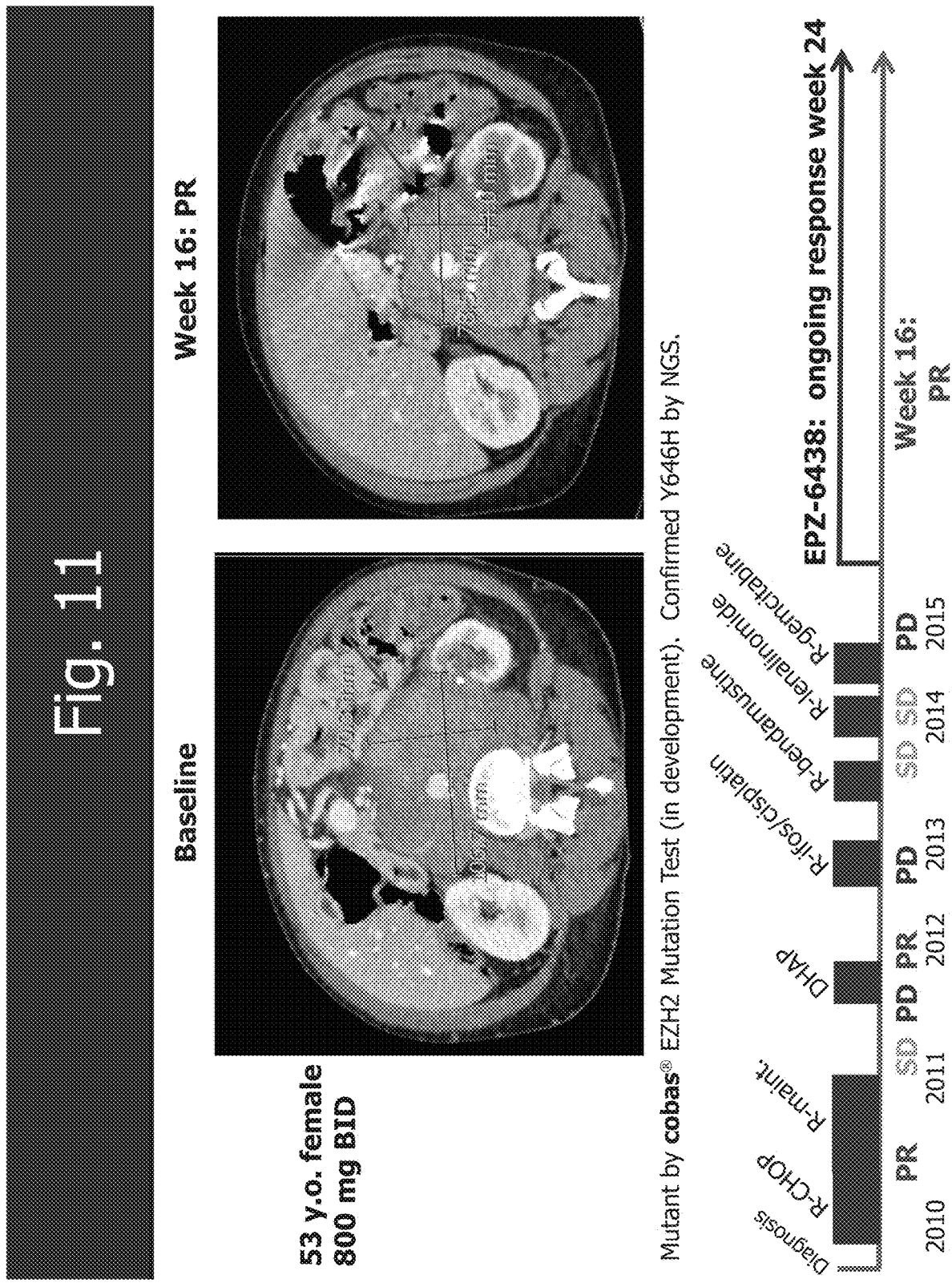

EZH2 INHIBITORS FOR TREATING LYMPHOMA

RELATED APPLICATIONS

This application is a continuation of U.S. patent application Ser. No. 16/454,835, filed Jun. 27, 2019 (now abandoned), which is a continuation of U.S. patent application Ser. No. 16/181,747, filed Nov. 6, 2018 (now abandoned), which is a continuation of U.S. patent application Ser. No. 15/319,535, filed Dec. 16, 2016 (now U.S. Pat. No. 10,166,238), which is a U.S. National Phase Application, filed under 35 U.S.C. § 371, of International Application No. PCT/US2015/036310, filed Jun. 17, 2015, which claims the benefit of and priority to U.S. Patent Application Nos. 62/013,522, filed Jun. 17, 2014; and 62/036,265, filed Aug. 12, 2014. The contents of each of these applications are hereby incorporated by reference in their entireties.

BACKGROUND OF THE INVENTION

EZH2, a histone methyltransferase, has been associated with various kinds of cancers. Specifically, mutations and and/or overactivity of EZH2 are found in a range of cancers, such as lymphomas, leukemias and breast cancer. There is an ongoing need for new agents as EZH2 inhibitors for use in anticancer treatment.

SUMMARY OF THE INVENTION

In one aspect, the present disclosure features a method for the treatment or prevention of non-Hodgkin's lymphoma (NHL) in a subject in need thereof. The method includes administration of a therapeutically effective amount of an EZH2 inhibitor to said subject.

The method can include one or more of the following features.

In one embodiment, the NHL is selected from diffuse large B-cell lymphoma (DLBCL), a germinal center-derived lymphoma, a non-germinal center-derived lymphoma, follicular lymphoma (FL), primary mediastinal large B-cell lymphoma (PMBCL), marginal zone lymphoma (MZL), Burkitt's lymphoma and other non-Hodgkin's lymphoma subtype.

In one embodiment, the NHL is a germinal center-derived lymphoma.

In one embodiment, the NHL is a non-germinal center-derived lymphoma.

In one embodiment, the NHL is follicular lymphoma.

In one embodiment, the NHL is PMBCL.

In one embodiment, the NHL is marginal zone lymphoma.

In one embodiment, the NHL is Burkitt's lymphoma.

In one embodiment, the NHL is other Non-Hodgkin's lymphoma subtype.

In one embodiment, the NHL is an EZH2 wild type B-cell lymphoma, e.g., the NHL cells having non-mutated, wild-type EZH2 protein.

In one embodiment, the NHL is an EZH2 mutant B-cell lymphoma, e.g., the NHL cells having mutant EZH2 protein.

In certain embodiments, the non-germinal center-derived lymphomas is Activated B-Cell (ABC) lymphoma.

In one embodiment, the non-germinal center B-cell lymphoma is an EZH2 wild type B-cell lymphoma, e.g., the lymphoma cells having non-mutated, wild-type EZH2 protein.

In another embodiment, the non-germinal center B-cell lymphoma is an EZH2 mutant B-cell lymphoma, e.g., the lymphoma cells having mutant EZH2 protein.

In one embodiment, the germinal center-derived lymphoma is an EZH2 wild type B-cell lymphoma, e.g., the lymphoma cells having non-mutated, wild-type EZH2 protein.

In another embodiment, the germinal center-derived lymphoma is an EZH2 mutant B-cell lymphoma, e.g., the lymphoma cells having mutant EZH2 protein.

In one embodiment, the follicular lymphoma (FL), primary mediastinal large B-cell lymphoma (PMBCL), or marginal zone lymphoma (MZL) is an EZH2 wild type germinal center B-cell lymphoma, e.g., the germinal center B-cell lymphoma cells having non-mutated, wild-type EZH2 protein.

In another embodiment, the follicular lymphoma (FL), primary mediastinal large B-cell lymphoma (PMBCL), or marginal zone lymphoma (MZL) is an EZH2 mutant germinal center B-cell lymphoma, e.g., the germinal center B-cell lymphoma cells having mutant EZH2 protein.

In one embodiment, the EZH2 inhibitor is administered orally.

In one embodiment, the subject is a human being.

In one embodiment, the EZH2 inhibitor is EPZ-6438 (tazemetostat), having the following formula:

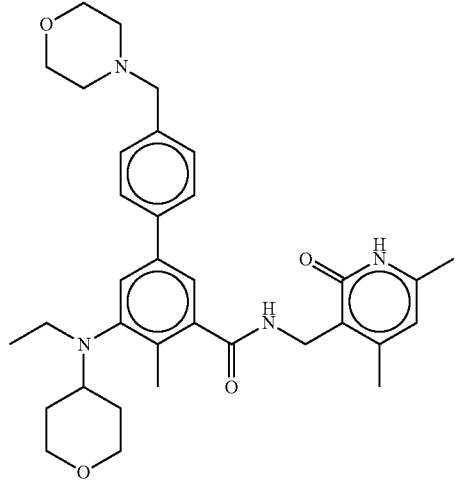

or a pharmaceutically acceptable salt thereof.

In one embodiment, the EZH2 inhibitor is administered to the subject at a dose of approximately 100 mg to approximately 3200 mg daily.

In one embodiment, the EZH2 inhibitor is administered to the subject at a dose of approximately 100 mg BID to approximately 1600 mg BID.

In one embodiment, the EZH2 inhibitor is administered to the subject at a dose of approximately 100 mg BID, 200 mg BID, 400 mg BID, 800 mg BID, or 1600 mg BID.

In one embodiment, the EZH2 inhibitor is either compound (A), (B), (C), or (D):

(A)
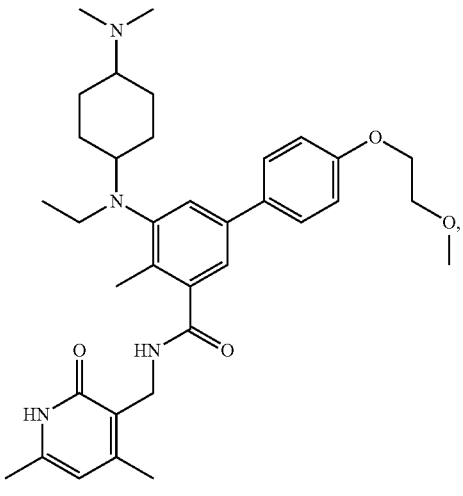

(B)
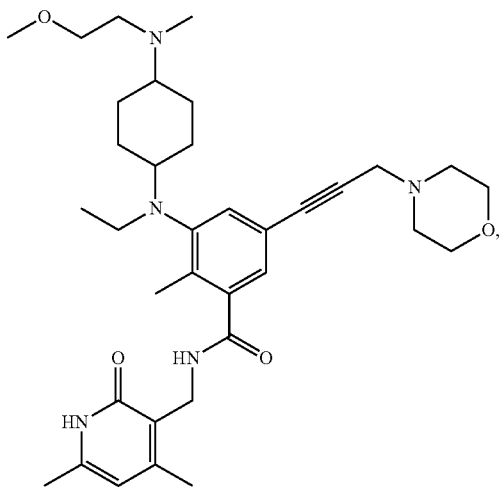

(C)
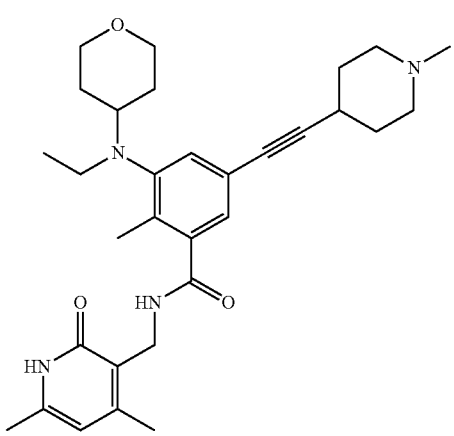

, or (D)
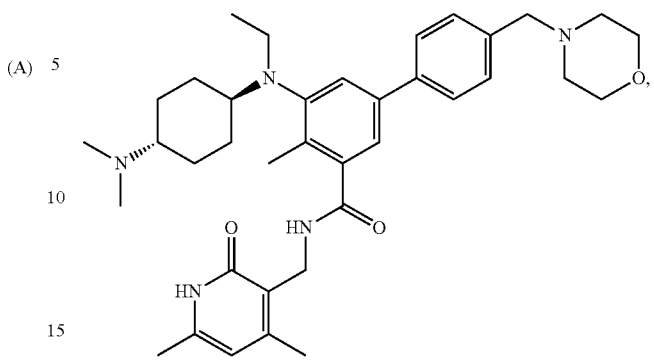

or pharmaceutically acceptable salts or solvates thereof.

Any of the above aspects and embodiments can be combined with any other aspect or embodiment.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE DRAWINGS

The above and further features will be more clearly appreciated from the following detailed description when taken in conjunction with the accompanying drawings.

FIG. 1 shows the summary of first-in-human phase 1 trial with tazemetostat (EPZ-6438) E7438-G000-001 (NCT01897571).

FIG. 2 shows the patient tumor types.

FIG. 3 shows the NHL patient demographics.

FIG. 6 shows the adverse events of the trial.

FIG. 7 shows the overall best responses in NHL patients.

FIG. 8 shows the target lesion activity.

FIG. 9 shows the CR (complete response) in primary mediastinal B-cell lymphoma.

FIG. 10 shows the CR in follicular lymphoma with wild type EZH2.

FIG. 11 shows the response in DLBCL with mutant EZH2 lymphoma (Y646H).

DETAILED DESCRIPTION OF THE INVENTION

Figure 4:
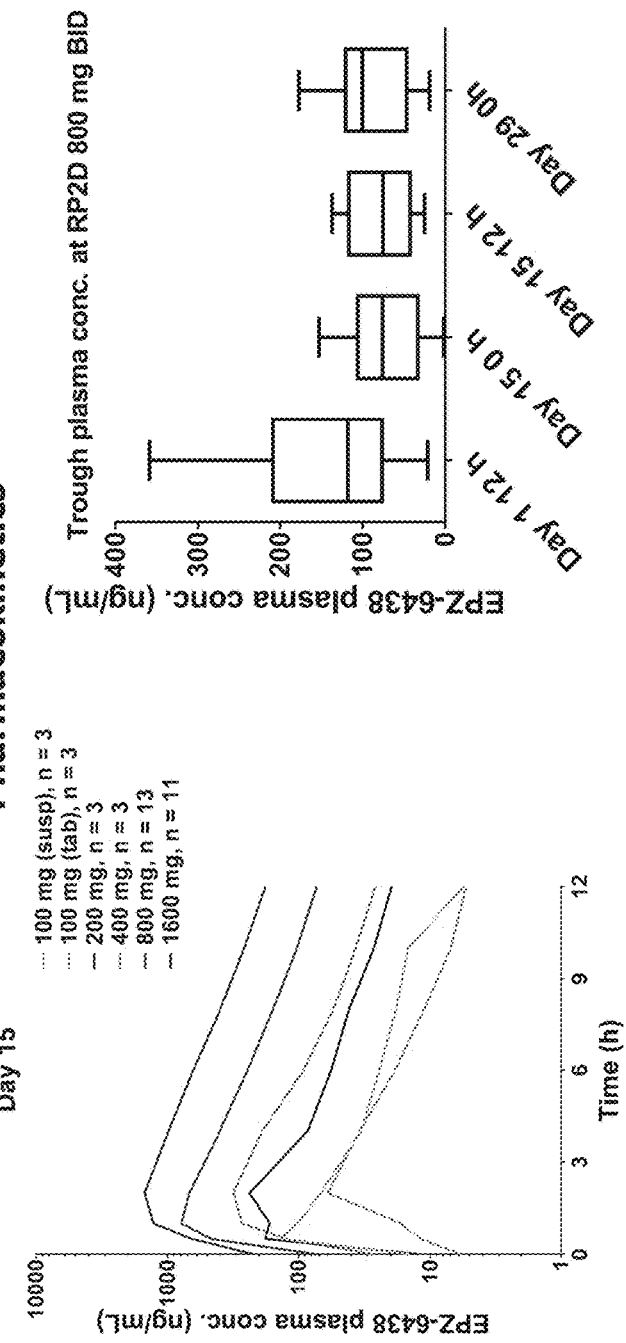
FIG. 4 shows the pharmacokinetics of tazemetostat (EPZ-6438).

EZH2 is a histone methyltransferase that is the catalytic subunit of the PRC2 complex which catalyzes the monothrough tri-methylation of lysine 27 on histone H3 (H3-K27). Histone H3-K27 trimethylation is a mechanism for suppressing transcription of specific genes that are proximal to the site of histone modification. This trimethylation is known to be a cancer marker with altered expression in cancer, such as prostate cancer (see, e.g., U.S. Patent Application Publication No. 2003/0175736; incorporated herein by reference in its entirety). Other studies provided evidence for a functional link between dysregulated EZH2 expression, transcriptional repression, and neoplastic transformation. Varambally et al. (2002) *Nature* 419(6907):624-9 Kleer et al. (2003) *Proc Natl Acad Sci USA* 100(20):11606-11.

EZH2 methylation activity plays an important role in the regulation and activation of germinal center B-cells. EZH2 protein levels increase following the activation of B-cells. Following activation, B-cells take residence in the germinal center of lymphoid organs, wherein somatic hypermutation occurs, a process associated with the repression of anti-apoptotic genes and check point regulators. EZH2 methylating events target genes that are involved in B-cell proliferation, differentiation and maturation, including CDKN1A (role in cellular proliferation), PRDM1 (role in B-cell differentiation) and IRF4 (role in B-cell differentiation).

Following the maturation and exit of B-cells from the germinal center, there is a reduction of the levels of EZH2 within the B-cells. However, EZH2 presence and activity after B-cell maturation is associated with several kinds of lymphomas including germinal center B-cell lymphoma, among others.

Aberrant activation or misregulation of EZH2 is found in many common subtypes of non-Hodgkin lymphoma (NHL): diffuse large B cell lymphoma (DLBCL), germinal center B-cell like diffuse large B-cell lymphoma (GCB DLBCL), non-germinal center B-cell like diffuse large B-cell lymphoma including activated-B cell lymphoma (ABC DLBCL), Burkitt's lymphoma and other subtypes of non-Hodgkin lymphoma. Aberrant activation of or misregulation EZH2 is also found in follicular lymphoma (FL), Primary Mediastinal Large B-Cell Lymphoma (PMBCL) and marginal zone lymphoma (MZL).

Genetic alterations within the EZH2 gene are associated with altered histone methylation patterns. EZH2 mutations leading to the conversion of amino acid Y641 (equivalent to Y646, catalytic domain), to either F, N, H, S or C results in hypertrimethylation of H3K27 and drives lymphomagenesis. Additional genetic alterations that affect the methylation of H3K27 include EZH2 SET-domain mutations, overexpression of EZH2, overexpression of other PRC2 subunits, loss of function mutations of histone acetyl transferases (HATs), and loss of function of MLL2. Cells that are heterozygous for EZH2 Y646 mutations result in hypertrimethylation of H3K27 relative to cells that are homozygous wild-type (WT) for the EZH2 protein, or to cells that are homozygous for the Y646 mutation.

An aspect of the present invention relates to a method for treating or alleviating a symptom of a NHL in a subject in need thereof by administering to the subject a therapeutically effective amount of an EZH2 inhibitor. An aspect of the present invention relates to a method for treating or alleviating a symptom of NHL in a subject in need thereof by administering to the subject a therapeutically effective amount of an EZH2 inhibitor. Another aspect of the present invention relates to a method for treating or alleviating a symptom of GCB DLBCL in a subject in need thereof by administering to the subject a therapeutically effective amount of an EZH2 inhibitor. In yet another aspect the present invention relates to a method for treating or alleviating a symptom of a FL, PMBCL, or MZL in a subject in need thereof by administering to the subject a therapeutically effective amount of an EZH2 inhibitor. The subject suitable for the method of treatment described herein can either express a mutant EZH2 or a wild-type EZH2 or has a mutation in the EZH2 gene or has a wild-type EZH2 gene.

As described herein, inhibition of EZH2 activity significantly abrogates the division of the malignant cells.

In one embodiment, the EZH2 inhibitor is administered orally.

In one embodiment, the subject is a human being.

In any of the above aspects or embodiments, the invention also relates to methods for detecting levels of histone methylation, e.g., H3K27 trimethylation, in a skin biopsy. Histone methylation is detected prior to initiation of treatment, while the subject is receiving treatment, and/or after treatment has concluded.

The mutant EZH2 described herein refers to a mutant EZH2 polypeptide or a nucleic acid sequence encoding a mutant EZH2 polypeptide. In certain embodiments the mutant EZH2 comprises one or more mutations in its substrate pocket domain. For example, the mutation may be a substitution, a point mutation, a nonsense mutation, a missense mutation, a deletion, or an insertion. Methods for detecting EZH2 mutations have been described in PCT/US11/051258, PCT/US13/030565, US20150099747, each of which is incorporated herein by reference in its entirety.

For purposes of this application, a Y641 mutant of human EZH2, and, equivalently, a Y641 mutant of EZH2, is to be understood to refer to a human EZH2 in which the amino acid residue corresponding to Y641 of wild-type human EZH2 is substituted by an amino acid residue other than tyrosine.

Compounds suitable for the methods disclosed herein are described in U.S. Publications 20120264734, and 20140107122 the contents of which are hereby incorporated by reference in their entireties. The compounds of suitable for administration as part of a combination therapy with one or more other therapeutic agents or treatment modality, suitable to be administered together, sequentially, or in alternation.

In one embodiment, the compound suitable for the methods disclosed herein is EPZ-6438 (tazemetostat):

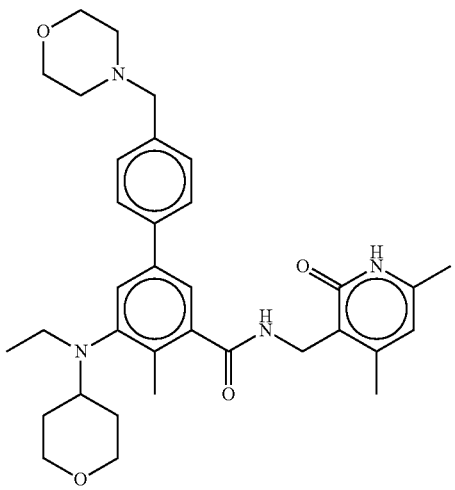

or a pharmaceutically acceptable salt thereof.

EPZ-6438 or a pharmaceutically acceptable salt thereof, as described herein, is potent in targeting both WT and mutant EZH2. EPZ-6438 is orally bioavailable and has high selectivity to EZH2 compared with other histone methyltransferases (i.e. >20,000 fold selectivity by Ki). Importantly, EPZ-6438 has target methyl mark inhibition that results in the killing of genetically defined cancer cells in vitro. Animal models have also shown sustained in vivo efficacy following inhibition of target methyl mark. Clinical trial results described herein also demonstrate the safety and efficacy of EPZ-6438.

In one embodiment, EPZ-6438 or a pharmaceutically acceptable salt thereof is administered to the subject at a dose of approximately 100 mg to approximately 3200 mg daily, such as about 100 mg BID to about 1600 mg BID (e.g., 100 mg BID, 200 mg BID, 400 mg BID, 800 mg BID, or 1600 mg BID), for treating a NHL. On one embodiment the dose is 800 mg BID.

In some embodiments, a compound (e.g., EZH2 inhibitor) that can be used in any methods presented here is:

(A)

(B)

(C)

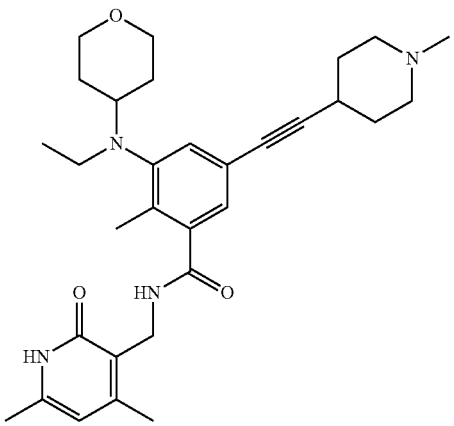

(D)

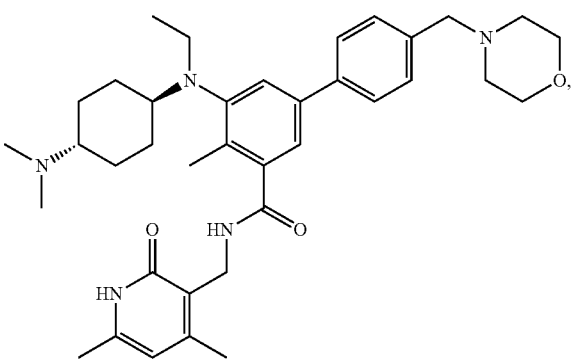

or stereoisomers thereof or pharmaceutically acceptable salts and solvates thereof.

In certain embodiments, a compound that can be used in any methods presented here is Compound E:

(E)

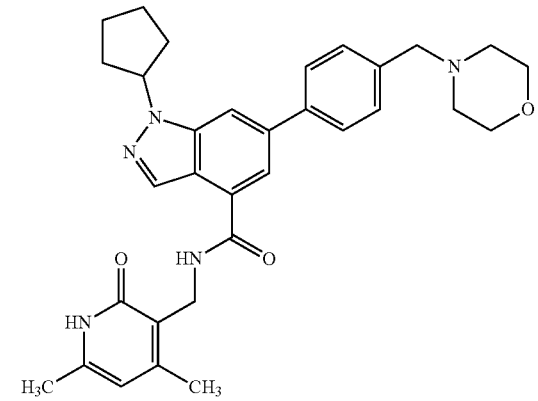

or pharmaceutically acceptable salts thereof.

In some embodiments, a compound (e.g., EZH2 inhibitor) that can be used in any methods presented here is GSK-126 having the following formula:

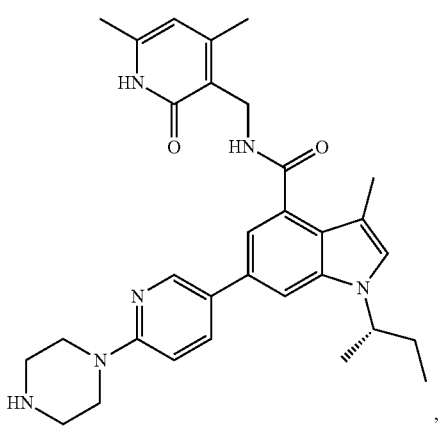 [SMILES: CC[C@H](C)n1cc(C)c2c(C(=O)NCc3c(C)cc(C)[nH]c3=O)cc(-c3ccc(N4CCNCC4)nc3)cc21]

stereoisomers thereof, or pharmaceutically acceptable salts or solvates thereof.

In certain embodiments, a compound that can be used in any methods presented here is Compound F:

(F)

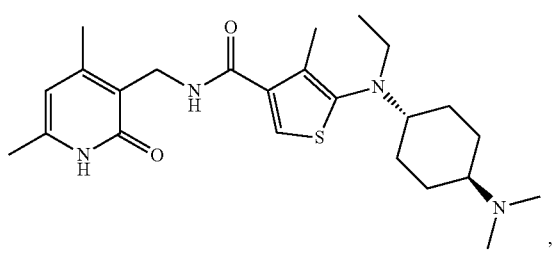

or stereoisomers thereof or pharmaceutically acceptable salts and solvates thereof.

In certain embodiments, a compound (e.g., EZH2 inhibitor) that can be used in any methods presented here is any of Compounds Ga-Gc:

(Ga)

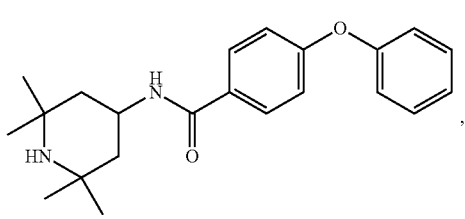

(Gb)

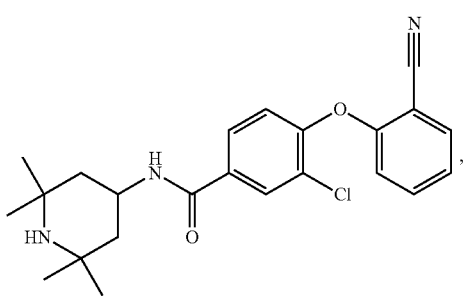

(Gc)

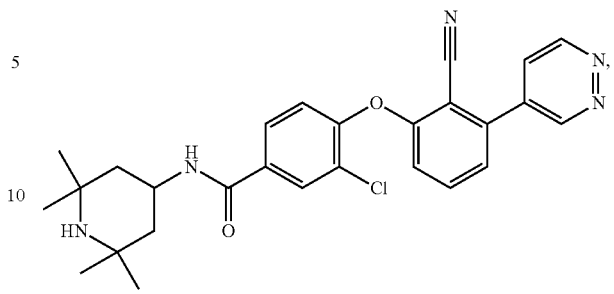

or a stereoisomer, pharmaceutically acceptable salt or solvate thereof.

In certain embodiments, a compound (e.g., EZH2 inhibitor) that can be used in any methods presented here is CPI-1205 or GSK343.

In one embodiment, the compound disclosed herein is the compound itself, i.e., the free base or "naked" molecule. In another embodiment, the compound is a salt thereof, e.g., a mono-HCl or tri-HCl salt, mono-HBr or tri-HBr salt of the naked molecule.

Compounds disclosed herein that contain nitrogens can be converted to N-oxides by treatment with an oxidizing agent (e.g., 3-chloroperoxybenzoic acid (mCPBA) and/or hydrogen peroxides) to afford other compounds suitable for any methods disclosed herein. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds disclosed herein can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds disclosed herein may be depicted as different chiral isomers or geometric isomers. It should also be understood that when compounds have chiral isomeric or geometric isomeric forms, all isomeric forms are intended to be included in the scope of the disclosure, and the naming of the compounds does not exclude any isomeric forms.

Furthermore, the structures and other compounds discussed in this invention include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

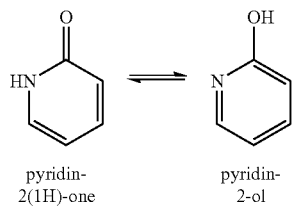

pyridin-2(1H)-one     pyridin-2-ol

It is to be understood that the compounds disclosed herein may be depicted as different tautomers. It should also be understood that when compounds have tautomeric forms, all tautomeric forms are intended to be included in the scope of the disclosure, and the naming of the compounds does not exclude any tautomer form.

The compounds disclosed herein include the compounds themselves, as well as their salts and their solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms. In the salt form, it is understood that the ratio of the compound to the cation or anion of the salt can be 1:1, or any ration other than 1:1, e.g., 3:1, 2:1, 1:2, or 1:3.

Additionally, the compounds disclosed herein, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are aryl- or heteroaryl-substituted benzene compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

In certain aspects, "combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In another aspect, a composition disclosed herein, or a pharmaceutically acceptable salt, solvate, analog or derivative thereof, may be administered in combination with radiation therapy. Radiation therapy can also be administered in combination with a composition disclosed herein and another chemotherapeutic agent described herein as part of a multiple agent therapy.

A "pharmaceutical composition" is a formulation containing a compound in a form suitable for administration to a subject. A compound disclosed herein and one or more other therapeutic agents described herein each can be formulated individually or in multiple pharmaceutical compositions in any combinations of the active ingredients. Accordingly, one or more administration routes can be properly elected based on the dosage form of each pharmaceutical composition. Alternatively, a compound disclosed herein and one or more other therapeutic agents described herein can be formulated as one pharmaceutical composition.

In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition disclosed herein is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition disclosed herein can be administered to a subject in many of the well-known methods currently used for chemotherapeutic treatment. For example, for treatment of cancers, a compound disclosed herein may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. For example, the therapeutically effective amount of an EZH2 inhibitor can be different for a patient having an EZH2 wild type germinal center B-cell lymphoma than for a patient having an EZH2 mutant germinal center B-cell lymphoma. Therapeutically effective amounts for a given situation can be determined by routine experimentation that is within the skill and judgment of the clinician.

In certain embodiments the therapeutically effective amount of each pharmaceutical agent used in combination will be lower when used in combination in comparison to monotherapy with each agent alone. Such lower therapeutically effective amount could afford for lower toxicity of the therapeutic regimen.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds disclosed herein may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms disclosed herein are dictated by and directly dependent on the unique characteristics of the active compound and the particular therapeutic effect to be achieved.

In therapeutic applications, the dosages of the EZH2 inhibitor compounds described herein, or the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The composition disclosed herein is capable of further forming salts. The composition disclosed herein is capable of forming more than one salt per molecule, e.g., mono-, di-, tri-. All of these forms are also contemplated within the scope of the claimed invention.

As used herein, "pharmaceutically acceptable salts" refer to derivatives of the compounds disclosed herein wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates), of the same salt.

The composition disclosed herein may also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The composition, or pharmaceutically acceptable salts or solvates thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds can be found in *Remington: the Science and Practice of Pharmacy,* $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

As used herein, a "subject in need thereof" is a subject having a NHL or a subject having an increased risk of developing such disorder relative to the population at large. A subject in need thereof can have a precancerous condition. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

The subject includes any human subject who has been diagnosed with, has symptoms of, or is at risk of developing NHL including DLBCL, GCB DLBCL, non-germinal center DLBCL including ABC DLBCL, FL, PMBCL, and MZL. The subject disclosed herein includes any human subject expressing a mutant EZH2 or WT EZH2 or has a mutation in the EZH2 gene or has a wild-type EZH2 gene. For example, a mutant EZH2 comprises one or more mutations, wherein the mutation is a substitution, a point mutation, a nonsense mutation, a missense mutation, a deletion, or an insertion or any other EZH2 mutation described herein.

A subject in need thereof may have refractory or resistant cancer. "Refractory or resistant cancer" means cancer that does not respond to treatment. The cancer may be resistant at the beginning of treatment or it may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In certain embodiments the prior therapy is monotherapy. In certain embodiments the prior therapy is combination therapy.

In some embodiments, a subject in need thereof may have a secondary cancer as a result of a previous therapy. "Secondary cancer" means cancer that arises due to or as a result from previous carcinogenic therapies, such as chemotherapy.

The subject may also exhibit resistance to EZH2 histone methyltransferase inhibitors or any other therapeutic agent.

The invention also features a method of selecting a therapy for a subject having a lymphoma including DLBCL, GCB DLBCL, non-germinal center DLBCL, ABC DLBCL, FL, PMBCL, and MZL.

The method includes the steps of: detecting the presence or absence of one or more EZH2 mutations described herein in a sample from the subject; and selecting, based on the presence or absence of the one or more EZH2 mutations, a therapy for treating the lymphoma. In one embodiment, the therapy includes administering to the subject a therapeutically effective amount of an EZH2 inhibitor described herein. An EZH2 mutation or absence thereof can be detected using any suitable method known in the art.

The methods and uses described herein may include steps of detecting the presence or absence of one or more EZH2 mutations described herein in a sample from a subject in need thereof prior to and/or after the administration of a composition disclosed herein (e.g., a composition comprising a compound disclosed herein or pharmaceutically acceptable salts thereof, alone or in combination with one or more second therapeutic agents) to the subject.

The present invention provides personalized medicine, treatment and/or cancer management for a subject having or at risk of having a germinal center-derived lymphoma, by genetic screening of one or more EZH2 mutations described herein in the subject. For example, the present invention provides methods for treating or alleviating a symptom of a germinal center-derived lymphoma in a subject in need thereof by determining responsiveness of the subject to a therapy and when the subject is responsive to the therapy, administering to the subject a composition disclosed herein. Once the responsiveness of a subject is determined, a therapeutically effective amount of a composition, for example, a composition comprising a compound disclosed herein or pharmaceutically acceptable salts thereof, alone or in combination with one or more second therapeutic agents, can be administered. The therapeutically effective amount of a composition can be determined by one of ordinary skill in the art.

As used herein, the term "responsiveness" is interchangeable with terms "responsive", "sensitive", and "sensitivity", and it is meant that a subject is showing therapeutic responses when administered a composition disclosed herein, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered a composition disclosed herein, e.g., tumor cells or tumor tissues of the subject undergo apoptosis and/or necrosis, and/or display reduced growing, dividing, or proliferation.

By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

As used herein, "candidate compound" refers to a compound disclosed herein, or a pharmaceutically acceptable salt or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound disclosed herein, or a pharmaceutically acceptable salt or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "treating" or "treat" describes the management and care of a patient for the purpose of combating a disease, condition, or disorder and includes the administration of a compound disclosed herein, or a pharmaceutically acceptable salt or solvate thereof, to alleviate the symptoms or complications of a disease, condition or disorder, or to eliminate the disease, condition or disorder.

A composition disclosed herein, or a pharmaceutically acceptable salt or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions disclosed herein leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound disclosed herein, or a pharmaceutically acceptable salt, solvate, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound disclosed herein, or a pharmaceutically acceptable salt, solvate, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound disclosed herein, or a pharmaceutically acceptable salt or solvate thereof, acts selectively on a cancer or precancerous cell but not on a normal cell. Preferably, a compound disclosed herein, or a pharmaceutically acceptable salt or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A composition disclosed herein, e.g., a composition comprising any compound disclosed herein or pharmaceutically acceptable salt thereof, can modulate the activity of a molecular target (e.g., a target protein methyltransferase). Modulating refers to stimulating or inhibiting an activity of a molecular target. Preferably, a compound disclosed herein, or a pharmaceutically acceptable salt or solvate thereof, modulates the activity of a molecular target if it stimulates or inhibits the activity of the molecular target by at least 2-fold relative to the activity of the molecular target under the same conditions but lacking only the presence of said compound. More preferably, a compound disclosed herein, or a pharmaceutically acceptable salt or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A composition disclosed herein does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound disclosed herein, or a pharmaceutically acceptable salt or solvate thereof, demonstrates a minimum of a fourfold differential, preferably a tenfold differential, more preferably a fifty fold differential, in the dosage required to achieve a biological effect. Preferably, a compound disclosed herein, or a pharmaceutically acceptable salt or solvate thereof, demonstrates this differential across the range of inhibition, and the differential is exemplified at the $IC_{50}$, i.e., a 50% inhibition, for a molecular target of interest.

Administering a composition disclosed herein to a cell or a subject in need thereof can result in modulation (i.e., stimulation or inhibition) of an activity of a protein methyltransferase of interest.

Administering a compound disclosed herein, e.g., a composition comprising any compound disclosed herein or pharmaceutically acceptable salt thereof, and one or more other therapeutic agents, such as prednisone, to a cell or a subject in need thereof results in modulation (i.e., stimulation or inhibition) of an activity of an intracellular target (e.g., substrate). Several intracellular targets can be modulated with the compounds disclosed herein, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a composition disclosed herein, or a pharmaceutically acceptable salt or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a composition disclosed herein, or a pharmaceutically acceptable salt or solvate thereof, can induce or activate cell death selectively in cancer cells. Administering to a subject in need thereof a compound disclosed herein, or a pharmaceutically acceptable salt or solvate thereof, can induce or activate cell death selectively in cancer cells. Contacting a cell with a composition disclosed herein, or a pharmaceutically acceptable salt or solvate thereof, can induce cell death selectively in one or more cells affected by a cell proliferative disorder. Preferably, administering to a subject in need thereof a composition disclosed herein, or a pharmaceutically acceptable salt or solvate thereof, induces cell death selectively in one or more cells affected by a cell proliferative disorder.

The present disclosure relates to a method of treating or preventing cancer by administering a composition disclosed herein, or a pharmaceutically acceptable salt or solvate thereof, to a subject in need thereof, where administration of the composition disclosed herein, or a pharmaceutically acceptable salt or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention.

Example 1

EPZ-6438 Clinical Study

The phase 1 trial enrolled patients with relapsed/refractory solid tumors and B cell lymphoma. The study employed a standard 3+3 dose escalation design with two planned dose expansion cohorts and clinical pharmacology sub-studies. The primary endpoint was determination of a recommended phase 2 dose or MTD with standard secondary endpoints.

The patients enrolled included 19 patients with NHL of which 13 patients have DLBCL. Cell-of origin testing was intended for all NHL patients, however, 3 DLBCL patients had insufficient tissue to permit determination of germinal center vs. non-germinal center status. EZH2 mutation testing was centrally performed for 14 NHL patients by the Cobas® test (Roche). One lymphoma patient whose tumor has been treated to date carries an EZH2 mutation. For the solid tumor patients, attention has been given to recruiting patients with INI1-deficient tumors due to the oncogenic role of EZH2 in these tumors.

NHL patients on study were heavily pre-treated with 85% having received three or more prior systemic therapies and nearly half receiving four or more prior regimens. 37% were refractory to their most recent prior regimen and five patients had a prior transplant.

The pharmacokinetics of EPZ-6438 are characterized by rapid absorption and a terminal half-life of 3 to 5 hours (FIG. 4). The drug displays dose-proportional linear PK at steady state throughout the entire dosing range. While a decrease in AUC between the first dose and day 15 was observed, there was no further reduction in systemic exposure beyond that time, as evidenced by pre-dose $C_{trough}$ levels in the right panel.

Figure 5:
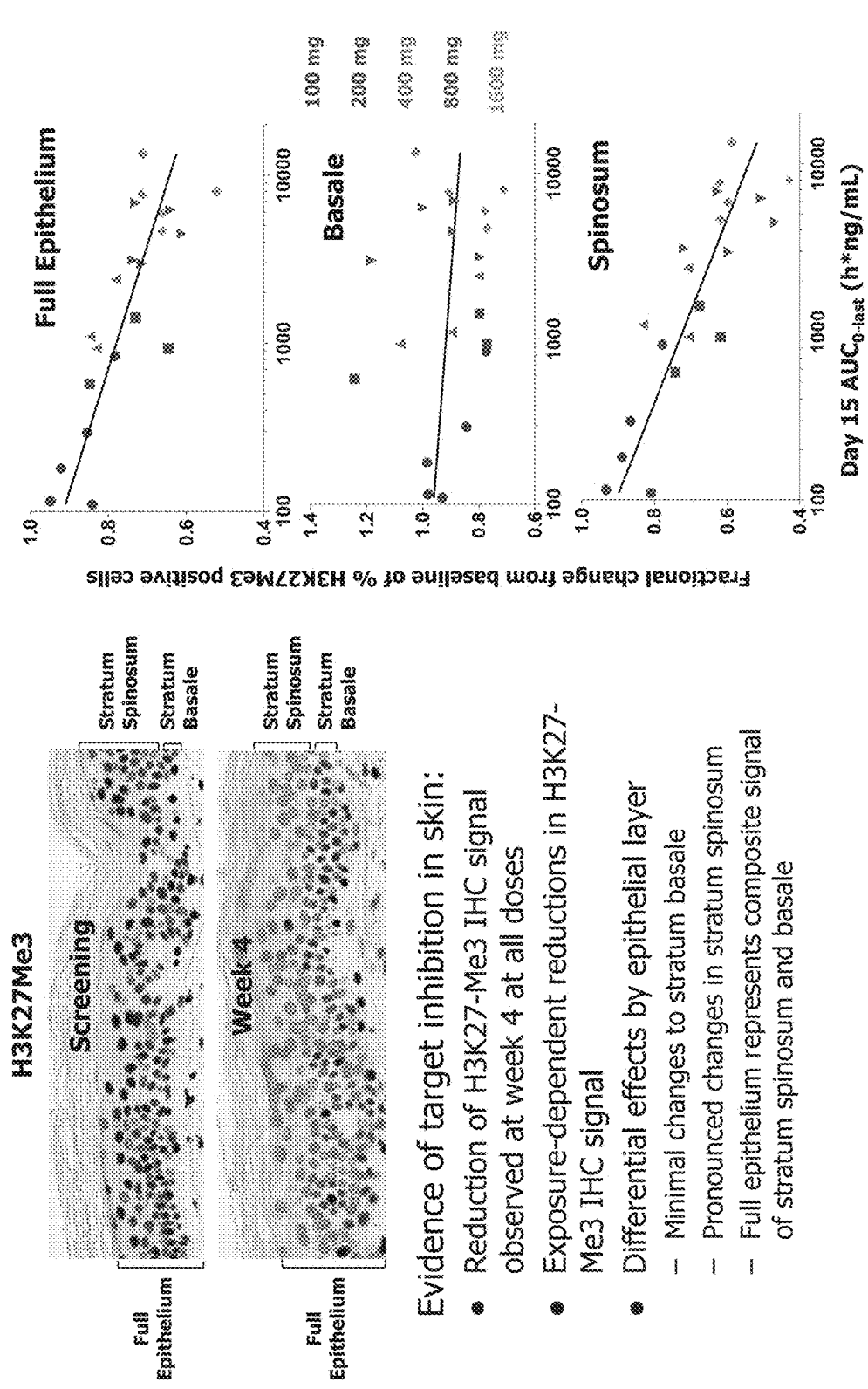
FIG. 5 shows the PK-PD: EZH2 inhibition in surrogate tissue.

FIG. 5 shows the pre- and post-dose skin biopsies were collected to assess pharmacodynamics in a surrogate tissue through the measurement of tri-methyl H3K27 levels by immunohistochemistry. It was previously shown that dose-dependent reduction of tri-methyl H3K27 levels across the full thickness of skin as demonstrated in the top right panel. With further refined quantitation by using image analysis to assess H3K27 signal in different layers of the skin; a much greater reduction of tri-methyl H3K27 signal was observed in the spinosum layer versus the basal layer which does not change appreciably.

These differences in pharmacodynamic response between the different layers of skin highlight the potential for variability in the kinetics for tri-methyl H3K27 turnover, even in cells of the same tissue.

EPZ-6438 is well-tolerated with the most common adverse events being asthenia, anorexia, anemia, dyspnea and nausea across the entire population (FIG. 6).

- Grade 3 or greater adverse events were observed in fewer than a third of patients.
- Grade 3 or greater treatment-related adverse events were observed in only 5 patients.
- The only DLT observed was thrombocytopenia which occurred at 1600 mg.
- One patient required a dose reduction for thrombocytopenia. One patient discontinued drug for grade 4 neutropenia. Both of these patients were treated in the 800 mg expansion cohort.
- Seven patients had dose interruptions. Of these, 6 were from a reversible toxicity and resumed study agent at prior dose without further issue.

FIG. 7 shows that of 15 evaluable NHL patients, 9 have had an objective response.

- In DLBCL, objective responses were seen in 5 of 9 patients. Of these, one patient remained on study at over 18 months and an additional patient with an EZH2 mutation remained on study at 6 months.
- In follicular lymphoma, 3 of 5 patients achieved objective responses with two patients on study at 12 months.
- One patient with marginal zone nodular lymphoma remained on study with a gradually improving partial response approaching one year on therapy.
- One feature of EPZ-6438's anti-tumor activity in NHL is a gradual, but prolonged reduction in tumor mass. This results in an evolution of objective response which can occur through 10 months on study. Patients may have a prolonged period of SD with gradual tumor shrinkage before becoming a PR. And the same may be seen before a PR becomes a CR. This pattern of response was observed across all subtypes of NHL studied to date.

FIG. 9 shows a 23 year old male with primary mediastinal B-cell lymphoma who became a CR by week 40 with a negative PET, despite being refractory to multiple intensive rituximab+chemotherapy regimens. He remained in CR at week 78.

FIG. 10 shows a male with multiply refractory follicular lymphoma as another example of evolution of response. His pen-orbital tumor reached criteria for PR at week 16 and then CR by week 32. He remained in CR at week 60.

FIG. 11 shows a patient with a tumor bearing an EZH2 mutation. She has an aggressive DLBCL and was very heavily pre-treated with six prior regimens and without an objective response for the last 3 years. Her scans revealed a dramatic response to tazemetostat with a 52% reduction of a very large abdominal mass by week 16. She remained in PR through 24 weeks on study.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for treating marginal zone lymphoma (MZL) in a subject comprising administering an EZH2 inhibitor to the subject.
2. The method of claim 1, wherein the EZH2 inhibitor is administered orally.
3. The method of claim 1, wherein the subject is a human.
4. The method of claim 3, wherein the EZH2 inhibitor is EPZ-6438 having the following formula:

or a pharmaceutically acceptable salt thereof.

5. The method of claim 4, wherein the EZH2 inhibitor is administered to the subject at a dose of about 100 mg to about 3200 mg daily.
6. The method of claim 4, wherein the EZH2 inhibitor is administered to the subject at a dose of about 100 mg BID to about 1600 mg BID.
7. The method of claim 4, wherein the EZH2 inhibitor is administered to the subject at a dose of about 100 mg BID, 200 mg BID, 400 mg BID, 800 mg BID, or 1600 mg BID.
8. The method of claim 7 wherein the EZH2 inhibitor is administered to the subject at a dose of 800 mg BID.
9. The method of claim 3, wherein the EZH2 inhibitor is:

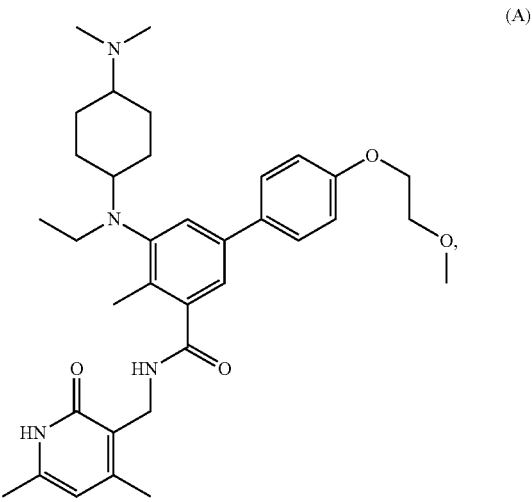 [SMILES: CCN(c1cc(-c2ccc(OCCOC)cc2)cc(C(=O)NCc2c(C)cc(C)[nH]c2=O)c1C)C1CCC(N(C)C)CC1]

(A)

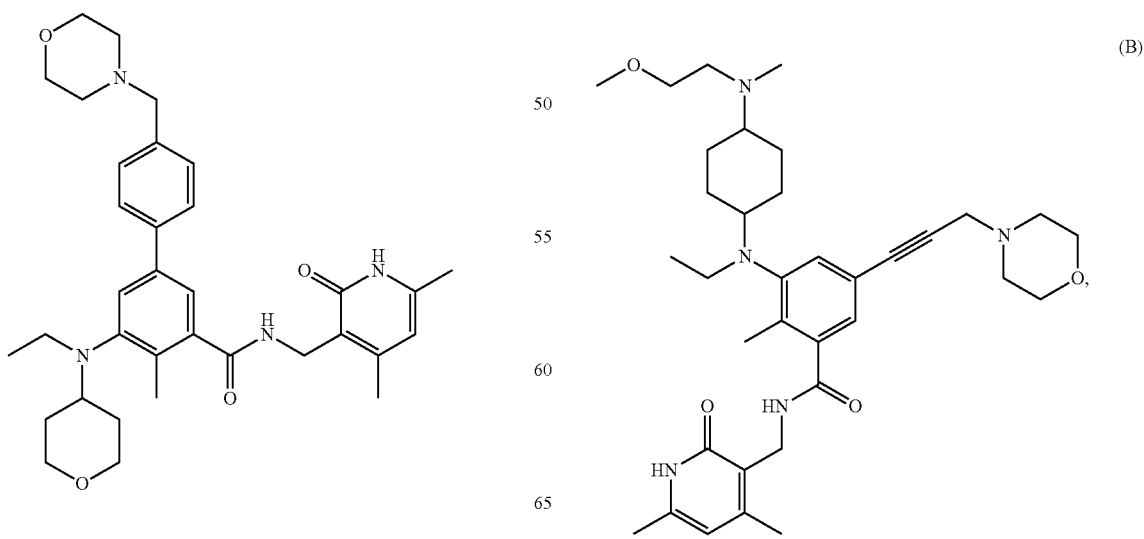

(B)

-continued
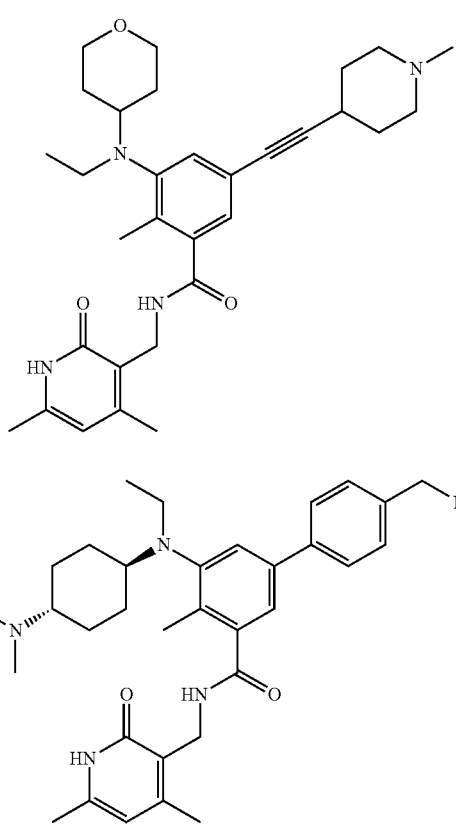
10. The method of claim 9, wherein the EZH2 inhibitor is:
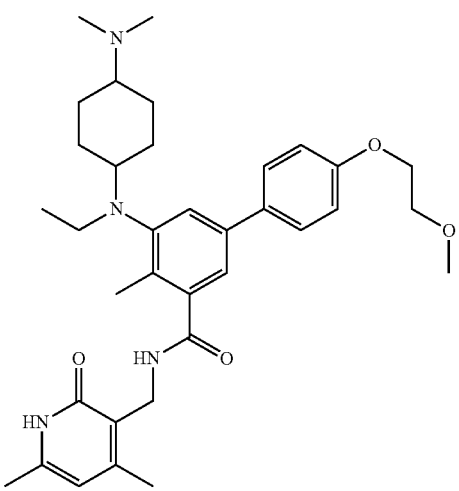
or a pharmaceutically acceptable salt thereof.
or a pharmaceutically acceptable salt thereof.
* * * * *